US008765975B2

(12) United States Patent
Hutchenson et al.

(10) Patent No.: US 8,765,975 B2
(45) Date of Patent: Jul. 1, 2014

(54) PRODUCTION OF DIHYDRONEPETALACTONE

(75) Inventors: Keith W. Hutchenson, Lincoln University, PA (US); Scott Christopher Jackson, Wilmington, DE (US); Leo Ernest Manzer, Wilmington, DE (US); Mark A. Scialdone, West Grove, PA (US); Mayis Seapan, Landenberg, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 682 days.

(21) Appl. No.: 12/519,770

(22) PCT Filed: Dec. 20, 2007

(86) PCT No.: PCT/US2007/025987
§ 371 (c)(1),
(2), (4) Date: Nov. 19, 2009

(87) PCT Pub. No.: WO2008/079252
PCT Pub. Date: Jul. 3, 2008

(65) Prior Publication Data
US 2010/0168447 A1    Jul. 1, 2010

Related U.S. Application Data

(60) Provisional application No. 60/876,568, filed on Dec. 21, 2006.

(51) Int. Cl.
*C07D 311/02* (2006.01)

(52) U.S. Cl.
USPC ........................................................ 549/283

(58) Field of Classification Search
USPC ........................................................ 549/283
See application file for complete search history.

(56) References Cited

U.S. PATENT DOCUMENTS

| | | | |
|---|---|---|---|
| 4,416,881 A | 11/1983 | McGovern | |
| 4,476,147 A | 10/1984 | Hall | |
| 4,496,467 A | 1/1985 | Munteanu | |
| 4,869,896 A | 9/1989 | Coulston | |
| 6,013,255 A | 1/2000 | Edens | |
| 6,462,015 B1 | 10/2002 | Weiss | |
| 6,524,605 B1 | 2/2003 | Coats | |
| 6,623,694 B1 | 9/2003 | Ferguson | |
| 6,673,756 B2 | 1/2004 | Sonnenberg | |
| 7,067,677 B2 * | 6/2006 | Manzer ..................... | 549/283 |
| 7,067,678 B2 | 6/2006 | Scialdone | |
| 7,232,844 B2 | 6/2007 | Hallahan et al. | |
| 7,250,174 B2 | 7/2007 | Lee | |
| 7,435,851 B2 | 10/2008 | Scialdone | |
| 7,820,145 B2 | 10/2010 | Tamarkin | |
| 2003/0062357 A1 | 4/2003 | Schneider et al. | |
| 2003/0079786 A1 | 5/2003 | Diana et al. | |
| 2003/0191047 A1 | 10/2003 | Hallahan | |
| 2003/0235601 A1 | 12/2003 | Hallahan | |
| 2004/0024054 A1 | 2/2004 | Haenke | |
| 2004/0127553 A1 | 7/2004 | Hallahan | |
| 2005/0137252 A1 | 6/2005 | Scialdone | |
| 2005/0239875 A1 | 10/2005 | Scialdone | |
| 2005/0244441 A1 | 11/2005 | Courtois | |
| 2006/0148842 A1 | 7/2006 | Scialdone | |
| 2006/0201391 A1 | 9/2006 | Scialdone | |
| 2006/0223878 A1 | 10/2006 | Scialdone | |
| 2006/0228387 A1 | 10/2006 | Scialdone | |
| 2007/0077262 A1 | 4/2007 | Scialdone | |
| 2007/0264297 A1 | 11/2007 | Scialdone | |
| 2008/0305135 A1 | 12/2008 | Kroepke | |
| 2010/0034906 A1 | 2/2010 | Gonzalez | |
| 2010/0092404 A1 | 4/2010 | Hutchenson | |
| 2010/0145077 A1 | 6/2010 | Jackson | |
| 2010/0145078 A1 | 6/2010 | Fisher | |
| 2010/0168447 A1 | 7/2010 | Hutchenson | |
| 2010/0261915 A1 | 10/2010 | Gonzalez | |

FOREIGN PATENT DOCUMENTS

| | | |
|---|---|---|
| WO | 03079786 | 2/2003 |
| WO | 03084946 | 10/2003 |
| WO | WO 2005/034626 | 4/2005 |

OTHER PUBLICATIONS

Regnier et al. Phytochemistry, 1967, 6, 1281-1289.*
De Pooter et al. Flavour and Fragrance Journal, 1988, 3, 155-159.*
Jefson et al., Chemical Defense of a Rove Beetle, Journal of Chemical Ecology, 1983, vol. 9, pp. 159-180.
Regnier et al., Studies on the Composition of the Essential Oils of Three *Nepeta* Species, Phytochemistry, 1967, vol. 6, pp. 1281-1289.
Waller et al., Metabolism of Nepetalactone and Related Compounds in *Nepeta catarial*. And Components of Its Bound Essential Oil, Proc. Oklahoma Acad. Sci., 1984, vol. 64, pp. 49-56.
De Pooter et al., The Essential Oils of Five *Nepeta* Species, Flavour and Fragrance Journal, 1988, vol. 3, pp. 155-159.
Handjieva et al., Constituents of Essential Oils From *Nepeta ctaria* L., N. Grandiflora M.B. and N. Nuda L., J. Essential Oil Res., 1996, vol. 8, pp. 639-643 Ordered Jun. 29 2010.
Nishimuru, The Handbook of Heterogeneous Catalytic Hydrogenation for Orgnic Synthesis, John Wiley, 2001, Book Not Included.
International Search Report, PCT/US2007/025987, Dated May 6, 2008.
Meinwald, The Degradation of Nepetalactone, Journal of the American Chemical Society, 1954, vol. 76, pp. 4571-4573.
Tanimori et. al., Total Synthesis of (+) Dihydronepetalactone, Agric. Biol. Chem., 1991, vol. 55:1181-11832.

(Continued)

*Primary Examiner* — Nizal Chandrakumar

(57) ABSTRACT

This invention provides a process for producing dihydronepetalactone using mixtures comprising both trans-cis nepetalactone and cis-trans nepetalactone. A reaction mixture comprising trans-cis nepetalactone and cis-trans nepetalactone is first contacted with hydrogen in the presence of at least one hydrogenation catalyst under conditions that optimise the preferential conversion of trans-cis nepetalactone to dihydronepetalactone. Cis-trans nepetalactone is subsequently converted to dihydronepetalactone by contact with hydrogen in the presence of at least one hydrogenation catalyst.

7 Claims, No Drawings

(56) References Cited

OTHER PUBLICATIONS

Fleming et. al., Sterocontrol in Organic Synthesis Using Silicon-Containing Compounds, A Synthesis of (+) Dihydronepetalactone using the SE2 reaction of an Allysilane, J. Chem. Soc., Perkin Trans, 1998, vol. 1:2645-2649.

Wolinsky et. al., Syntheses of the Dihydronepetalactones, J. Org. Chem., 1972, vol. 37:3376-3378.

G. Schultz et al., Natural Insect Repellents: Activity Against Mosquitoes and Cockroaches, ACS symposium Series, 2006, vol. 927:168-181.

G.W.K. Cavill et. al., Defensive and Other Secretions of the Australlian Cocktail Ant, Iridomyrmex nitidiceps, Tetrahedron, 1982, vol. 38:1931-1938.

Chris Peterson et. al Insect Repellents—Past, Present and Future, Pesticide Outlook, Aug. 2001.

Edmund J. Eisenbraun et al., (4AS,7S,7AR)-Nepetalactam and (4AS,7S,7AR)-2-[(3R,4R,4AR,7AR)-Octahydro-4,7-Dimethyl-1-Oxocyclopenta[C]Pyran-3-Yl]Nepetalactam: Nitrogen Analogues of Nepetalactone and Nepetalic-Anhydride, J. Org. Chem., vol. 53:3968-3972, 1988.

Regnier et al, Nepetalactone and Eipnepetalactone From Nepeta Cataria L., Phytochemistry, 1967, vol. 6:1271-1280.

T. Eisner, Science, 1964, vol. 146:1318-1320.

* cited by examiner

PRODUCTION OF DIHYDRONEPETALACTONE

This application claims the benefit of U.S. Provisional Application No. 60/876,568, filed 21 Dec. 2006, which is incorporated in its entirety as a part hereof for all purposes.

TECHNICAL FIELD

This invention is related to a process for producing dihydronepetalactone.

BACKGROUND

Dihydronepetalactone is a useful compound that has been shown to have insect repellent properties [see, for example, Jefson et al, *J. Chemical Ecology* (1983) 9; 159-180; and WO 03/79786]. Methods for the production of dihydronepetalactone are known from sources such as Regnier et al [Phytochemistty (1967) 6:1281-1289]; Waller and Johnson [*Proc. Oklahoma. Acad. Sci.* (1984) 64:49-56]; and U.S. Pat. No. 7,067,677 (Manzer). Those methods have, in general, described the production of mixtures comprising isomers of dihydronepetalactone by contacting purified nepetalactones with hydrogen in the presence of a catalyst.

A need nevertheless remains for a method for converting mixtures comprising trans-cis nepetalactone and cis-trans nepetalactone to dihydronepetalactone with limited formation of the less desirable by-product puleganic acid.

SUMMARY

In one embodiment, this invention involves a process for preparing dihydronepetalactone by (a) contacting in a reaction mixture a starting amount of trans-cis nepetalactone (as described by the structure of Formula I) and a starting amount of cis-trans nepetalactone (as described by the structure of Formula II)

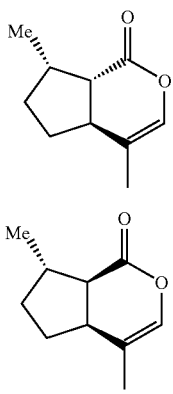

with hydrogen and a first solid hydrogenation catalyst at a first temperature or temperatures until the amount by weight of trans-cis nepetalactone in the reaction mixture is no more than about 50% of the starting amount thereof, to form a first product mixture; and (b) contacting the first product mixture with hydrogen and a second solid hydrogenation catalyst at a second temperature or temperatures to form a dihydronepetalactone; wherein the second temperature or temperatures are higher than the first temperature or temperatures.

In another embodiment, this invention involves a process for preparing dihydronepetalactone by (a) contacting a starting mixture comprising trans-cis nepetalactone (as described by the structure of Formula I) and cis-trans nepetalactone (as described by the structure of Formula II)

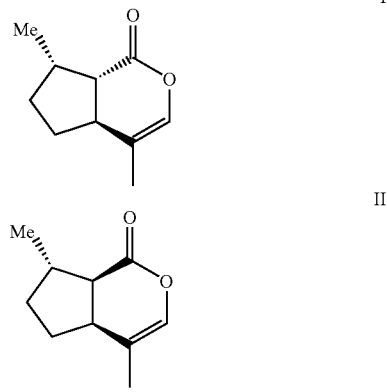

with hydrogen and a first solid hydrogenation catalyst, to form a first product mixture; and (b) contacting the first product mixture with hydrogen and a second solid hydrogenation catalyst to form a dihydronepetalactone; wherein the first and second catalysts are different.

In a further embodiment, this invention involves a process for preparing dihydronepetalactone by contacting a starting mixture comprising trans-cis nepetalactone (as described by the structure of Formula I) and cis-trans nepetalactone (as described by the structure of Formula II)

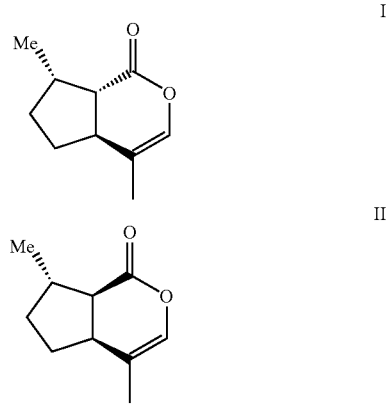

with hydrogen and a solid hydrogenation catalyst; wherein, in the starting mixture, the ratio of the content by weight of cis-trans nepetalactone to the content by weight of trans-cis nepetalactone is at least about 2/1.

DETAILED DESCRIPTION

Definitions:

In the description of the processes hereof, the following definitional structure is provided for certain terminology as employed in various locations in the specification:

The term "nepetalactone" refers to the compound having the general structure of Formula II:

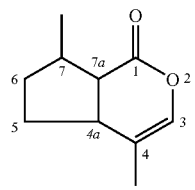

A preferred source of nepetalactone is catmint oil obtained from the plant genus *Nepeta*. Different species of *Nepeta* have been reported to possess different proportions of the stereoisomers of nepetalactone [Regnier et al, *Phytochemistry*, 6:1281-1289 (1967); DePooter et al, *Flavour and Fragrance Journal*, 3:155-159 (1988); Handjieva and Popov, *J. Essential Oil Res.*, 8:639-643 (1996)], two of which stereoisomers are as follow:

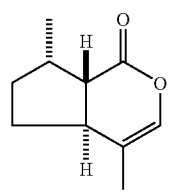

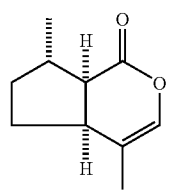

Dihydronepetalactones are defined, by Formula VII:

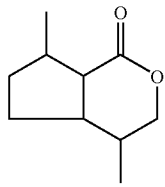

Formula II

Unless otherwise indicated, the term "dihydronepetalactone" refers to any mixture of dihydronepetalactone isomers. The molar or mass composition of each of these isomers relative to the whole dihydronepetalactone composition can be variable.

The term "puleganic acid" refers to a compound having the general structure of Formula III:

Formula III

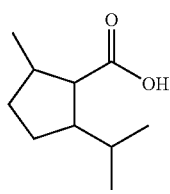

The term "catalyst" refers to a substance that affects the rate of the reaction but not the reaction equilibrium, and emerges from the process chemically unchanged.

The term "promoter" refers to an element of the periodic table, or alloys or compounds thereof, that is added to enhance the physical or chemical function of a catalyst. A promoter may be any element of the periodic table that could be added to a catalyst to enhance its activity or selectivity. A promoter can also be added to retard undesirable side reactions and/or affect the rate of the reaction. Catalysts, promoters and their use are additionally described in sources such as *The Handbook of Heterogeneous Catalytic Hydrogenation for Organic Synthesis* by Shigeo Nishimuru, John Wiley (2001), ISBN: G-471-39698-2. A "promoter metal" is promoter that is a metallic compound.

This invention relates to processes for producing dihydronepetalactone from mixtures comprising both trans-cis nepetalactone and cis-trans nepetalactone. A reaction mixture comprising trans-cis nepetalactone and cis-trans nepetalactone is first contacted with hydrogen in the presence of at least one hydrogenation catalyst under conditions that optimise the preferential conversion of trans-cis nepetalactone to dihydronepetalactone. In the second step of the process, the hydrogenation of cis-trans nepetalactone to dihydronepetalactone is optimized.

It has been found that trans-cis nepetalactone is reduced to the desired end-product dihydronepetalactone under less aggressive hydrogenation conditions, including lower temperatures, whereas under more aggressive hydrogenation conditions, including higher temperatures, trans-cis nepetalactone is converted to puleganic acid. Cis-trans nepetalactone is not appreciably converted to dihydronepetalactone under less aggressive hydrogenation conditions, including lower temperatures, whereas at more aggressive conditions, including higher temperatures, cis-trans-nepetalactone is converted to dihydronepetalactone without appreciable formation of puleganic acid.

The processes hereof thus provide a first hydrogenation reaction and a second hydrogenation reaction to prepare dihydronepetalactone from a mixture comprising both trans-cis and cis-trans nepetalactone.

First Hydrogenation Reaction:

In the first hydrogenation reaction, a reaction mixture containing a starting amount of trans-cis nepetalactone (as described by the structure of Formula IV) and a starting amount of cis-trans nepetalactone (as described by the structure of Formula V)

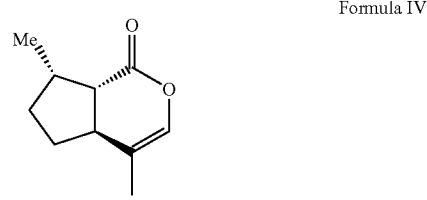

Formula IV

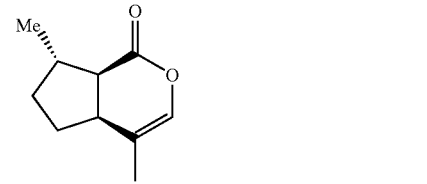

Formula V is contacted, optionally in the presence of a solvent, with hydrogen in the presence of at least one solid hydrogenation catalyst at a first temperature or temperatures until the amount by weight of trans-cis nepetalactone in the reaction mixture is no more than about 50% of the starting amount thereof, to form a first product mixture. In additional embodiments of the invention, the amount by weight of trans-cis nepetalactone in the reaction mixture may be no more than about 40%, or about 30%, or about 20%, or about 10%, or about 5%, or about 1%, of the starting amount thereof.

Correspondingly, as a result of the first hydrogenation reaction, the amount by weight of cis-trans nepetalactone in the reaction mixture is at least about 50% of the starting amount thereof, or is at least about 60%, or about 70%, or about 80%, or about 90%, or about 95%, or about 99%, of the starting amount thereof.

The length of time consumed until the selected extent of decrease (as described above) in the starting amount of trans-cis nepetalactone has occurred will vary according to the selections made for the reaction temperature, catalyst/promoter and rate of hydrogen feed. As a result of the first hydrogenation reaction, the reaction mixture may contain, for example, at least one dihydronepetalactone isomer.

The first hydrogenation reaction may be performed at one temperature or at several temperatures, including a range of temperatures. In one embodiment, the first hydrogenation reaction is carried out at a temperature or temperatures in the range of from about 0° C. to about 100° C. In another embodiment, the temperature(s) may be in the range of from about 0° C. to about 60° C., or from about 0° C. to about 50° C., or from about 10° C. to about 50° C. The first hydrogenation reaction is preferably performed at temperature(s) at which trans-cis nepetalactone, rather than cis-trans nepetalactone, is preferentially converted to dihydronepetalactone.

A solid hydrogenation catalyst as used in the first hydrogenation reaction may contain a catalytic metal selected from elements from, the group consisting of iron, ruthenium, rhenium, copper, osmium, cobalt, rhodium, iridium, nickel, palladium, platinum, alloys or compounds thereof; and combinations thereof. In one embodiment, the catalytic metal is selected from the group consisting of palladium, platinum, nickel; alloys or compounds thereof; and combinations thereof.

A promoter metal, where used, may be selected from the metals in Groups 3 through 8, 11 and 12 of the Periodic Table, including without limitation tin, zinc, copper, gold, silver, iron, molybdenum, alloys or compounds thereof and combinations thereof. Promoter metals may be used to affect the reaction, for example by increasing activity and catalyst lifetime. Promoter metals are typically used at up to about 2% by weight of the total weight of metals used in the reaction.

The catalyst used in hydrogenation may be supported or unsupported. A supported catalyst, is one in which the catalytic metal is deposited on a support material by any one of a number of methods, such as spraying, soaking or physical mixing, followed by drying, calcination, and if necessary, activation through methods such as reduction or oxidation/reduction. A supported catalyst may also be made by co-precipitation or blending of the active components and the support material followed by followed by drying, calcination, and if necessary, activation through methods such as reduction or oxidation/reduction. Materials frequently used, as a catalyst support are porous solids with high total surface areas (external and internal) which, can provide high concentrations of active sites per unit weight of catalyst. The catalyst support may enhance the function of the catalyst.

The catalyst support useful herein, can be any solid substance including, but not limited to, oxides of silica, alumina, titania, and combinations thereof; barium sulfate; calcium carbonate; carbons; and combinations thereof. The catalyst support can be in the form of powder, granules, pellets, extrudates, or the like.

In one embodiment, supported catalysts (comprising catalytic metal and catalyst support) useful in the hydrogenation may be selected from, the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, nickel on silica-alumina, ruthenium on carbon, ruthenium on silica, rhenium on alumina, ruthenium on carbon, ruthenium on alumina, ruthenium on silica, and combinations thereof; wherein the catalytic metal comprises from about 0.1% to about 70% by weight of the weight of the catalytic metal pins support.

In a preferred embodiment, combinations of catalytic metal and catalyst support useful for the invention are selected from the group consisting of palladium, on carbon, platinum on carbon, iridium on carbon, rhodium on carbon, ruthenium on carbon, iridium on silica, and combinations thereof.

For the process of the invention, the preferred content of the catalytic metal in a supported catalyst will depend on the choice of the catalyst and support. In one embodiment, the content of the catalytic metal in the supported catalyst may foe from about 0.1% to about 70% of the supported catalyst based on catalytic metal weight plus the support weight.

A catalyst that is not supported on a catalyst support material is an unsupported catalyst. An unsupported catalyst may be any porous structure, a powder such as platinum black or a Raney catalyst (Raney® catalytic products from W.R. Grace & Co., Columbia Md.), or combinations thereof. The active metals of Raney catalysts include nickel, copper, cobalt, iron, rhodium, ruthenium, rhenium, osmium, iridium, platinum, palladium; compounds thereof; and combinations thereof. At least one promoter metal may also be added to the base Raney metals to affect selectivity and/or activity of the Raney catalyst. Promoter metals for Raney catalysts may be selected from transition metals from Groups 3 through 8, 11 and 12 of the Periodic Table of the Elements, alloys or compounds thereof and combinations thereof. Examples of suitable promoter metals include chromium, molybdenum, platinum, rhodium, ruthenium, osmium, palladium, alloys or compounds thereof and combinations thereof, typically at up to 2% by weight of the total metal.

The catalyst, and promoter if used, selected for use in the first hydrogenation reaction will preferably be one that preferentially converts trans-cis nepetalactone to dihydronepetalactone rather than to puleganic acid, and/or preferentially converts trans-cis nepetalactone rather than cis-trans nepetalactone to dihydronepetalactone.

Contact in the reaction mixture of trans-cis nepetalactone and cis-trans nepetalactone with hydrogen in the presence of a solid hydrogenation catalyst may be carried oat in the presence of a solvent. Solvents useful for the process of the invention include without, limitation alcohols, such as ethanol or isopropanol, alkanes, such, as hexanes or cyclohexane; esters such as ethyl acetate; and ethers such as dioxane, tetrahydrofuran or diethyl ether.

The first product mixture may optionally be separated from the solid hydrogenation catalyst prior to the second hydrogenation step. Known methods of separation may be used for this purpose, and include distillation, decantation and filtration.

Second Hydrogenation Reaction:

in the second hydrogenation reaction, the first product mixture is contacted with hydrogen in the presence of at least one solid hydrogenation catalyst at a second, temperature or temperatures to form a second product mixture comprising at least one dihydronepetalactone isomer. The second temperature or temperatures are higher than the first temperature or temperatures. The second hydrogenation reaction is preferably performed at temperature(s) at which cis-trans nepetalactone, rather than trans-cis nepetalactone, is preferentially converted to dihydronepetalactone. In one embodiment, the second hydrogenation reaction is performed at a temperature(s) in the range of from about 50° C. to about 150° C., or in the range of from, greater than 60° C. to about 150° C.

The hydrogenation catalyst, and promoter if used, as used in the second hydrogenation reaction may be any of those as described above for use in the first hydrogenation reaction; and may be used in the same or similar amounts. The hydrogenation catalyst/promoter as used in the second hydrogenation reaction may be the same as, or different than, the hydrogenation catalyst/promoter as used in the first hydrogenation reaction. Preferably, the hydrogenation catalyst/promoter as used in the second hydrogenation reaction is different than the hydrogenation catalyst/promoter as used in the first hydrogenation reaction, and is a catalyst/promoter that preferentially converts cis-trans nepetalactone, rather than trans-cis nepetalactone, to dihydronepetalactone.

The hydrogen pressure useful for either the first or second hydrogenation reactions is from about 0.1 MPa to about 20.7 MPa. In one embodiment, the hydrogen is maintained at a pressure to achieve saturation levels of the hydrogen in the mixture at the temperature of the reaction.

The second product mixture obtained after the second hydrogenation reaction is separated from the hydrogenation catalyst. Methods of separation are well-known to those skilled in the art, and include distillation, decantation and filtration.

The process of the present invention may be carried out in batch in a single reactor, in sequential batch in a series of reactors, in reaction zones within one or more reactors, or in continuous mode in any of the equipment customarily employed for continuous processes. Different temperatures and/or different catalysts, for example, could be used in any two or more of the sequential zones or reactors provided that trans-cis nepetalactone is converted primarily to dihydronepetalactone rather than puleganic acid, and/or that a substantial amount of trans-cis nepetalactone is preferentially converted to dihydronepetalactone before cis-trans nepetalactone is converted.

In an alternative embodiment of the processes hereof, dihydronepetalactone may be produced in a single-stage process in which the starting material is predominantly cis-trans nepetalactone rather than trans-cis nepetalactone. In such a reaction, in the starting reaction mixture, the ratio of the content by weight of cis-trans nepetalactone to the content by weight of trans-cis nepetalactone may, for example, be at least about 1/1. In alternative embodiments, the ratio of the content, by weight of cis-trans nepetalactone to the content, by weight of trans-cis nepetalactone may be at least about 2/1, or at least about 3/1, or at least about 5/1, or at least about 10/1. The same catalyst/promoter(s), temperatures and hydrogen feed rates as described above for the second hydrogenation reaction may be used in this alternative process.

In a further embodiment hereof, the amount by weight of cis-trans nepetalactone in the reaction mixture is reduced to less than about 20% of the starting amount thereof. In alternative, embodiments, the amount by weight of cis-trans nepetalactone in the reaction mixture is reduced to less than about 10%, or leas than about 5%, of the starting amount thereof.

In a further embodiment of the processes hereof, the concentration of puleganic acid produced in the reaction is less than about 10% by weight of the total weight of the reaction, products. In another embodiment, the amount of puleganic acid produced in the reaction is less than about 5% by weight of the total weight of the reaction products. In a further embodiment of the processes hereof, the process produces in the product thereof puleganic acid in amount by weight that is less than about 10%, or less than about 5%, of the combined weight of the starting amount of trans-cis nepetalactone and the starting amount of cis-trans nepetalactone components.

The starting mixture comprising trans-cis nepetalactone and cis-trans nepetalactone may be obtained from plants of the genus *Nepeta*, for example *Nepeta cataria*. Oil comprising nepetalactone isomers, such as the trans-cis and cis-trans Isomers, can be obtained from *Nepeta* plants by various isolation processes, including but not limited to steam distillation, organic solvent extraction, microwave-assisted organic solvent extraction, supercritical fluid extraction, mechanical extraction and enfleurage (initial cold extraction into fats followed by organic solvent extraction). The oil can be used in the crude form, or the nepetalactones can be further purified from the oil by distillation, for example. In addition to trans-cis nepetalactone and cis-trans nepetalactone the mixture may comprise extraneous components, including unsaturated compounds such as carvones, limonenes and other monoterpenoids, and caryophyllenes and other sesquiterpenoids, that may be reduced by the process of the invention.

EXAMPLES

The advantageous attributes and effects of the processes hereof pay be seen in a series of examples, as described below. The embodiments of these processes on which the examples are based are representative only, and the selection of those embodiments to illustrate the invention does not indicate that materials, conditions, arrangements, components, reactants, techniques or configurations not described in these examples are not suitable for practicing these processes, or that subject matter not described in these examples is excluded from the scope of the appended claims and equivalents thereof.

In the examples, the following abbreviations are used: GC is gas chromatography; GC-MS is gas chromatography-mass spectrometry; FID is flame ionization detector; NMR is nuclear magnetic resonance; C is Centrigrade, MPa is mega Pascal; rpm is revolutions per minute; mL, is milliliter; CMO is catmint oil; wt % is weight percent; TOS is time on stream; NPL is nepetalactone; c,t-NPL is cis-trans nepetalactone; t,c-nepetalactone is trans-cis nepetalactone, DHN is dihydronepetalactone; h is hour; conc. is concentration; conv is conversion; temp is temperature; press is pressure, ° C. is degrees Centigrade.

Determination of Catmint Oil Constituents and the Hydrogenated Compounds Thereof:

Samples were diluted with an internal standard solution and injected on a DB FFAP column using an HP5890 (Agilent Technologies, Palo Alto, Calif.) GC equipped with a FID detector. The injection and detector temperatures were 250° C. The temperature of the column was linearly ramped from 50° C. to 250° C. for 20 min and held at 250° C. for the duration of the run. A split mode inlet was used. Peak identification and relative response factors of the major components were determined using calibration standards of nepetalactone, dihydronepetalactone and puleganic acid.

Examples 1-14

A sample of commercially-available catmint oil, extracted by steam distillation of herbaceous material from the catmint *Nepeta cataria*, was obtained from George Thacker Sons, Alberta, Canada. Ethanol, hexanes and 2-propanol were obtained from Aldrich.

The catalysts were obtained commercially from the following manufacturers: ESCAT 142 and ESCAT 268; Engelhard Corp. (Iselin, N.J.); Rh/C: Acros (Hampton, N.H.); Ru/C: Strem Chemicals, Inc. (Newburyport, Mass.)

The example reactions were conducted in a 50 ml stirred batch autoclave reactor charged with a solution of catmint oil and a powder catalyst. The reactor was sealed and then flushed and evacuated with nitrogen several times to remove oxygen. These flushes were followed by two rapid flushes with hydrogen to minimize residual nitrogen in the reactor. The reactor was equipped with a magnetically-coupled gas entrainment agitator which was rotated at about 1000 rpm during the reaction. The reactor temperature was controlled either by flowing a propylene glycol/water mixture from a recirculating bath through an external coil, or by use of an external electrical band heater. Hydrogen was continuously fed to the reactor during the course of the run to maintain a specified pressure as hydrogen was consumed by the reaction. Following the reaction, the reactor was cooled via the external cooling coil and vented. Product analysis was conducted by gas chromatography (GC) as described above using 1,2-dibromobenzene as the internal standard added post reaction. Additional reaction conditions and the corresponding reaction profiles showing conversion of nepetalactones to dihydronepetalactones and key byproducts are provided below for the individual examples.

Example 1 (Comparative)

Hydrogenation of Catmint Oil at 100° C.

At 100° C., both cis-nepetalactone and trans-nepetalactone are converted to dihydronepetalactone with a high yield loss to puleganic acid.

| CMO Conc. (wt %) | Solvent | Catalyst | Catalyst Charge (wt % of CMO) | $H_2$ Pressure (MPa) | TOS (h) | Temp. (° C.) | NPL Conv. (%) | c,t-NPL Conv. (%) | t,c-NPL Conv. (%) | DHN Yield (%) | Puleganic Acid Yield (%) |
|---|---|---|---|---|---|---|---|---|---|---|---|
| 50 | Ethanol | ESCAT 142 5% Pd/C | 10 | 8.46 | 0.17 | 102 | 20.8 | 13.6 | 22.8 | 85.9 | 6.8 |
| | | | | | 0.50 | 97 | 91.7 | 64.4 | 99.3 | 82.7 | 18.3 |
| | | | | | 1.00 | 98 | 97.3 | 88.8 | 100.0 | 81.1 | 18.6 |
| | | | | | 1.78 | 100 | 99.4 | 98.2 | 100.0 | 78.1 | 20.6 |
| | | | | | 2.75 | 100 | 99.7 | 99.3 | 100.0 | 72.7 | 25.4 |
| | | | | | 4.00 | 100 | 99.8 | 99.4 | 100.0 | 67.3 | 29.6 |
| | | | | | 5.18 | 101 | 99.8 | 99.4 | 100.0 | 62.7 | 33.3 |

Example 2

Two-Stage Process

This example shows the reaction being run first at 15° C. for 4 hours, followed by an additional 2 hours at 100° C. By conducting the reaction in two stages, the DHN yield was higher and the puleganic acid yield was reduced relative to that obtained at the single temperature of 100° C. as shown in Comparative Example 1.

| CMO Conc. (wt %) | Solvent | Catalyst | Catalyst Charge (wt. % of CMO) | $H_2$ Press. (MPa) | TOS (h) | Temp. (° C.) | NPL Conv. (%) | c,t-NPL Conv. (%) | t,c-NPL Conv. (%) | DHN Yield (%) | Puleganic Acid Yield (%) |
|---|---|---|---|---|---|---|---|---|---|---|---|
| 50 | Ethanol | ESCAT 142 5% Pd/C | 10 | 8.36 | 0.17 | 15 | 8.6 | 2.7 | 10.8 | 94.4 | 1.1 |
| | | | | | 0.50 | 15 | 15.0 | 3.3 | 19.4 | — | 1.4 |
| | | | | | 1.00 | 15 | 36.4 | 8.3 | 47.1 | 99.5 | 1.7 |
| | | | | | 1.88 | 15 | 64.2 | 19.2 | 81.4 | 97.6 | 2.5 |
| | | | | | 2.75 | 15 | 76.1 | 27.5 | 94.7 | 99.5 | 2.9 |
| | | | | | 4.00 | 15 | 82.7 | 40.2 | 99.3 | 98.7 | 3.2 |
| | | | | | 5.00 | 100 | 97.7 | 92.5 | 99.9 | 96.7 | 3.6 |
| | | | | | 5.17 | 101 | 99.3 | 98.0 | 100.0 | 96.8 | 3.7 |
| | | | | | 7.00 | 99 | 99.6 | 98.7 | 100.0 | 97.9 | 3.6 |

Examples 3-14

Two-Stage Process

These examples show the reaction being run under different conditions for CMO concentration, pressure, catalyst charge and catalyst, in the two-stage process.

| Example | CMO Conc. (wt %) | Solvent | Catalyst | Catalyst Charge (wt % of CMO) | $H_2$ Press. (MPa) | TOS (h) | Temp. (° C.) | NPL Conv. (%) | c,t-NPL Conv. (%) | t,c-NPL Conv. (%) | DHN Yield (%) | Puleganic Acid Yield (%) |
|---|---|---|---|---|---|---|---|---|---|---|---|---|
| 3 | 30 | Hexanes | ESCAT 142 5% Pd/C | 10 | 3.58 | 0.17 | 25 | 81.3 | — | 89.5 | 93.5 | 9.8 |
| | | | | | | 0.50 | 25 | 93.1 | — | 99.6 | 93.1 | 9.6 |
| | | | | | | 1.00 | 25 | 95.2 | 21.4 | 99.9 | 93.7 | 9.3 |
| | | | | | | 4.00 | 25 | 96.7 | 42.1 | 99.9 | 92.2 | 9.0 |

-continued

| Example | CMO Conc. (wt %) | Solvent | Catalyst | Catalyst Charge (wt % of CMO) | H₂ Press. (MPa) | TOS (h) | Temp. (° C.) | NPL Conv. (%) | c,t-NPL Conv. (%) | t,c-NPL Conv. (%) | DHN Yield (%) | Puleganic Acid Yield (%) |
|---|---|---|---|---|---|---|---|---|---|---|---|---|
| 4 | 10 | 2-Propanol | ESCAT 142 5% Pd/C | 10 | 3.47 | 0.17 | 25 | 9.3 | 5.7 | 11.0 | 44.8 | 4.9 |
|   |   |   |   |   |   | 0.50 | 25 | 12.2 | 1.8 | 16.7 | 95.2 | 7.5 |
|   |   |   |   |   |   | 1.00 | 25 | 24.3 | 5.0 | 32.7 | 92.2 | 5.3 |
|   |   |   |   |   |   | 2.00 | 25 | 41.7 | 8.5 | 56.2 | 94.6 | 3.4 |
|   |   |   |   |   |   | 3.00 | 25 | 55.1 | 13.8 | 73.2 | 92.0 | 2.7 |
|   |   |   |   |   |   | 6.00 | 25 | 72.2 | 22.9 | 93.8 | 87.8 | 8.4 |
| 5 | 20 | Ethanol | ESCAT 142 5% Pd/C | 10 | 3.50 | 0.17 | 25 | 9.5 | 4.3 | 11.5 | 63.8 | 4.5 |
|   |   |   |   |   |   | 1.00 | 25 | 37.4 | 9.5 | 47.8 | 86.7 | 2.8 |
|   |   |   |   |   |   | 2.00 | 25 | 55.8 | 14.3 | 71.4 | 83.2 | 7.6 |
|   |   |   |   |   |   | 3.00 | 25 | 63.0 | 17.8 | 80.0 | 82.8 | 7.6 |
|   |   |   |   |   |   | 6.00 | 25 | 79.9 | 26.7 | 100.0 | 81.6 | 6.8 |
| 6 | 20 | Ethanol | ESCAT 142 5% Pd/C | 10 | 3.51 | 0.17 | 50 | 27.7 | 9.0 | 34.7 | 78.1 | 3.9 |
|   |   |   |   |   |   | 1.00 | 50 | 79.2 | 24.0 | 100.0 | 79.1 | 7.4 |
|   |   |   |   |   |   | 2.00 | 50 | 32.6 | 37.1 | 100.0 | 85.0 | 7.4 |
|   |   |   |   |   |   | 6.00 | 50 | 90.2 | 66.5 | 100.0 | 87.8 | 7.3 |
| 7 | 20 | Ethanol | ESCAT 142 5% Pd/C | 10 | 3.51 | 0.17 | 48 | 53.1 | 17.5 | 66.5 | 77.1 | 11.6 |
|   |   |   |   |   |   | 0.50 | 50 | 76.1 | 29.2 | 93.8 | 77.6 | 11.9 |
|   |   |   |   |   |   | 1.00 | 50 | 82.7 | 38.6 | 99.6 | 83.4 | 12.9 |
|   |   |   |   |   |   | 2.00 | 90 | 91.8 | 72.0 | 100.0 | 84.1 | 12.1 |
|   |   |   |   |   |   | 6.00 | 101 | 99.8 | 99.8 | 100.0 | 82.5 | 11.2 |
| 8 | 20 | Ethanol | ESCAT 142 5% Pd/C | 10 | 3.49 | 0.17 | 26 | 28.3 | 8.1 | 35.8 | 80.1 | 4.2 |
|   |   |   |   |   |   | 1.03 | 25 | 75.7 | 24.4 | 94.8 | 82.2 | 8.0 |
|   |   |   |   |   |   | 2.00 | 25 | 81.1 | 33.2 | 99.3 | 84.2 | 8.2 |
|   |   |   |   |   |   | 4.05 | 99 | 99.6 | 98.7 | 100.0 | 86.9 | 7.7 |
|   |   |   |   |   |   | 6.00 | 100 | 99.9 | 99.7 | 100.0 | 87.3 | 7.8 |
| 9 | 20 | Ethanol | ESCAT 142 5% Pd/C | 10 | 8.04 | 0.17 | 25 | 42.7 | 11.1 | 54.3 | 85.7 | 3.2 |
|   |   |   |   |   |   | 1.00 | 25 | 79.4 | 29.3 | 98.1 | 89.5 | 2.8 |
|   |   |   |   |   |   | 1.50 | 25 | 81.9 | 35.5 | 99.4 | 89.6 | 2.8 |
|   |   |   |   |   |   | 3.00 | 98 | 98.0 | 93.5 | 100.0 | 89.8 | 3.3 |
|   |   |   |   |   |   | 6.00 | 99 | 99.9 | 99.7 | 100.0 | 91.6 | 3.2 |
| 10 | 50 | Ethanol | ESCAT 142 5% Pd/C | 1 | 8.65 | 0.47 | 15 | 0 | 0 | 0 | 0 | 0 |
|   |   |   |   |   |   | 2.75 | 15 | 0 | 0 | 0 | 0 | 0 |
|   |   |   |   |   |   | 4.03 | 100 | 9.4 | 6.4 | 2.0 | 90.3 | 2.4 |
|   |   |   |   |   |   | 5.80 | 99 | 24.8 | 15.2 | 21.8 | 86.7 | 3.9 |
|   |   |   |   |   |   | 6.90 | 100 | 41.6 | 26.3 | 42.7 | 89.7 | 4.3 |
| 11 | 50 | Ethanol | ESCAT 142 5% Pd/C | 3.5 | 8.44 | 0.50 | 15 | 6.5 | 1.4 | 0.5 | 105.6 | 1.1 |
|   |   |   |   |   |   | 1.00 | 15 | 13.8 | 3.3 | 10.7 | 103.1 | 1.7 |
|   |   |   |   |   |   | 1.75 | 15 | 21.1 | 5.1 | 20.9 | 106.0 | 2.1 |
|   |   |   |   |   |   | 2.83 | 15 | 28.4 | 6.3 | 31.3 | 107.4 | 2.1 |
|   |   |   |   |   |   | 4.00 | 15 | 35.7 | 8.7 | 41.3 | 100.4 | 1.9 |
| 12 | 50 | Ethanol | ESCAT 268 5% Pt/C | 10 | 8.36 | 0.50 | 27 | 43.8 | 12.0 | 53.7 | 82.1 | 17.0 |
|   |   |   |   |   |   | 1.00 | 25 | 65.4 | 19.6 | 81.1 | 91.4 | 11.5 |
|   |   |   |   |   |   | 2.00 | 24 | 81.9 | 31.0 | 97.7 | 90.0 | 8.9 |
|   |   |   |   |   |   | 3.00 | 24 | 83.3 | 36.9 | 97.8 | 93.7 | 9.4 |
|   |   |   |   |   |   | 3.32 | 96 | 93.3 | 76.1 | 98.7 | 95.2 | 9.4 |
|   |   |   |   |   |   | 3.82 | 100 | 99.5 | 98.6 | 99.8 | 100.6 | 11.1 |
| 13 | 50 | Ethanol | Acros 5% Rh/C | 10 | 8.51 | 0.17 | 25 | 5.3 | 13.7 | — | 3.2 | 7.0 |
|   |   |   |   |   |   | 0.50 | 25 | 3.8 | 7.3 | — | 2.5 | 9.7 |
|   |   |   |   |   |   | 1.00 | 28 | 78.6 | 44.8 | 89.0 | 52.1 | 43.1 |
|   |   |   |   |   |   | 2.00 | 25 | 99.5 | 98.3 | 99.9 | 56.0 | 40.7 |
|   |   |   |   |   |   | 5.50 | 100 | 99.9 | 99.7 | 100.0 | 39.9 | 51.8 |
| 14 | 50 | Ethanol | Stream Chem. 5% Ru/C | 10 | 8.48 | 0.17 | 26 | 8.3 | 10.6 | — | 43.3 | 35.6 |
|   |   |   |   |   |   | 0.50 | 25 | 30.8 | 22.3 | 18.8 | 27.0 | 64.7 |
|   |   |   |   |   |   | 1.00 | 25 | 49.5 | 29.1 | 47.2 | 35.8 | 65.7 |
|   |   |   |   |   |   | 2.00 | 25 | 85.8 | 46.8 | 97.7 | 35.2 | 59.2 |
|   |   |   |   |   |   | 3.00 | 25 | 93.4 | 76.0 | 98.6 | 39.6 | 60.5 |
|   |   |   |   |   |   | 3.40 | 95 | 100.0 | 100.0 | 100.0 | 39.6 | 56.5 |
|   |   |   |   |   |   | 3.90 | 101 | 99.9 | 99.8 | 100.0 | 28.8 | 63.1 |
|   |   |   |   |   |   | 5.40 | 99 | 99.9 | 99.9 | 100.0 | 30.5 | 65.3 |

Where a range of numerical values is recited herein, the range includes the endpoints thereof and all the individual integers and fractions within the range, and also includes each of the narrower ranges therein formed by all the various possible combinations of those endpoints and internal integers and tractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a con-zero value.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

A catalyst suitable for use herein may be selected as any one or more or all of the members of the whole population of catalysts described by name or structure above. A suitable catalyst may, however, also be selected as any one or more or all of the members of a subgroup of the whole population, where the subgroup may be any size (1, 2, 4 or 6, for example), and where the subgroup is formed by omitting any one or more of the members of the whole population as described above. As a result, the catalyst may in such instance not only be selected as one or more or all of the members of any subgroup of any sire that may be formed from the whole population of catalysts as described above, but the catalyst may also be selected in the absence of the members that have been omitted from, the whole population to form the subgroup. For example, in certain embodiments, the catalyst useful herein may be selected as one or more or all of the members of a subgroup of catalysts that excludes from the whole population ruthenium supported on titania, with or without the exclusion from, the whole population of other catalysts too.

What is claimed is:

1. A process for preparing dihydronepetalactone comprising:
    (a) contacting in a reaction mixture a starting amount of trans-cis nepetalactone (Formula I) and a starting amount of cis-trans nepetalactone (Formula II)

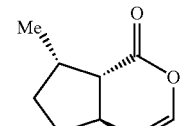

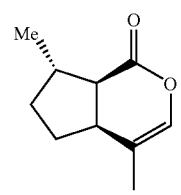

with hydrogen and a palladium on carbon catalyst at a first temperature or temperatures until the amount by weight of trans-cis nepetalactone in the reaction mixture is no more than about 50% of the starting amount thereof, to form a first product mixture; and
    (b) contacting the first product mixture with hydrogen and a palladium on carbon catalyst, at a second temperature or temperatures to form a dihydronepetalactone reaction product;
    wherein step (a) is performed at a temperature or temperatures in the range of from about 0° C. to 100° C., and step (b) is performed at a temperature or temperatures in the range of from 50° C. to 150° C.; and
    wherein the temperature or temperatures in step (b) are higher than the temperature or temperatures in step (a).

2. The process of claim 1 wherein step (a) is performed at a temperature or temperatures in the range of from about 0° C. to about 60° C., and step (b) is performed at a temperature or temperatures in the range of from greater than 60° C. to about 150° C.

3. The process of claim 1 wherein step (a) is performed at a temperature or temperatures in the range of from about 0° C to about 50° C, and step (b) is performed at a temperature or temperatures in the range of from greater than 60° C. to about 150° C.

4. The process of claim 1 wherein the amount by weight of trans-cis nepetalactone in the reaction mixture is no more than about 10% of the starting amount thereof.

5. The process of claim 1 wherein the hydrogen feed pressure is in the range of from about 0.1 MPa to about 20.7 MPa.

6. The process of claim 1 wherein, in the starting mixture, the ratio of the content by weight of cis-trans nepetalactone to the content by weight of trans-cis nepetalactone is at least about 2/1.

7. The process of claim 1 wherein the reaction product contains less than about 10 wt % puleganic acid.

* * * * *